US00PP08988P

United States Patent [19]

VandenBerg

[11] Patent Number: Plant 8,988

[45] Date of Patent: Nov. 22, 1994

[54] CHRYSANTHEMUM PLANT NAMED CHRISTINE

[75] Inventor: Cornelis P. VandenBerg, Salinas, Calif.

[73] Assignee: Yoder Brothers, Inc., Barberton, Ohio

[21] Appl. No.: 155,237

[22] Filed: Nov. 22, 1993

[51] Int. Cl.[5] ..... A01H 5/00

[52] U.S. Cl. ..... Plt./81

[58] Field of Search ..... Plt. 76, 80, 81, 82

*Primary Examiner*—Howard J. Locker

*Attorney, Agent, or Firm*—Foley & Lardner

[57] ABSTRACT

A Chrysanthemum plant named Christine particularly characterized by its flat capitulum form; decorative capitulum type; coral-red ray floret color; diameter across face of capitulum of 60 to 64 mm when fully opened; branching pattern is spreading and prolific, with 7 to 9 breaks after pinch when grown outside under natural daylength in fall flowerings and 5 breaks when grown in 10 cm pots for spring flowerings; natural season flower date of August 24 to September 2 when planting rooted cuttings on June 21 to 25 in Salinas, Calif., and of September 23 to October 5 when planting rooted cuttings June 11 to June 18 in Hightstown, N.J.; flowering response of 45 to 51 days after rooting in no light/no shade programs in spring in Salinas; plant height of 36 to 41 cm when grown in fall under natural daylength with no growth regulators in New Jersey, and 15 to 20 cm when grown in 10 cm pots in spring with no growth regulator applications; and durable, uniform performance.

3 Drawing Sheets

The present invention comprises a new and distinct cultivar of Chrysanthemum, botanically known as *Dendranthema grandiflora,* and referred to by the cultivar name Christine.

Christine, identified as 8302 (89-755001), was originated from a cross made by Cornelis P. VandenBerg in a controlled breeding program in Salinas, Calif., in 1988.

The female parent of Christine was an unnamed seedling identified as 5924 (84-M38004) and described as a flat decorative garden mum with a pink ray floret color with a diameter of capitulum of 64 mm. The female parent was discarded from all programs on May 23, 1988.

The male parent of Christine was an unnamed seedling, identified as 8431 (86-479004) and described as a bronze decorative garden mum with many disc florets and a diameter of capitulum of 44 mm. The male parent was discarded from all programs on Oct. 10, 1988.

Christine was discovered and selected as one flowering plant within the progeny of the stated cross by Cornelis P. VandenBerg in September 1989, in a controlled environment in Salinas, Calif.

The first act of asexual reproduction of Christine was accomplished when vegetative cuttings were taken from the initial selection in November 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Christine are firmly fixed and are retained through successive generations of asexual reproduction.

Christine has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were estabished in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Christine, which, in combination, distinguish this Chrysanthemum as a new and distinct cultivar:

1. Flat capitulum form.
2. Decorative capitulum type.
3. Coral-red ray floret color.
4. Diameter across face of capitulum of 60 to 64 mm when fully opened.
5. Branching pattern is spreading and prolific, with 7 to 9 breaks after pinch when grown outside under natural daylength in fall flowerings, and 5 breaks when grown in 10 cm pots for spring flowerings.
6. Natural season flower date of August 24 to September 2 when planting rooted cuttings on June 21 to 25 in Salinas, Calif., and September 23 to October 5 when planting rooted cuttings June 11 to June 18 in Hightstown, N.J.
7. Flowering response of 45 to 51 days after rooting in no light/no shade programs in spring in Salinas.
8. Plant height of 36 to 41 cm when grown in fall under natural daylength with no growth regulators in New Jersey, and 15 to 20 cm when grown in 10 cm pots in spring with no growth regulator applications.
9. Durable, uniform performance.

The accompanying photographic drawings show typical inflorescence and leaf characteristics of Christine, with the colors being as nearly true as possible with illustrations of this type.

Sheet 1 is a color photograph of Christine grown as a pinched garden mum under natural season outside conditions in Salinas, Calif. Plants were grown outside and dug and transplanted into 15 cm bulb pans at flowering time for photograph purposes.

Sheet 2 is a black and white photograph of three views of the inflorescence of Christine.

Sheet 3 is a black and white photograph showing the upper and under sides of the leaves of Christine at 3 stages of development (mature, intermediate and immature). In sheets 2 and 3 a measuring tape in centimeters has been added.

Of the commercial cultivars known to the inventor, the most similar in comparison to Christine is the cultivar identified as Grenadine, disclosed in U.S. Plant Pat. No. 5,338. Reference is made to attached Chart A, which compares certain characteristics of Grenadine.

Similar traits are capitulum form and type, branching pattern and natural season flower dates in fall flowerings. The ray floret color of Christine is described as coral-red, while the ray floret color of Grenadine is described as coral-bronze. In addition, when compared with Grenadine, Christine has a smaller diameter of capitulum, a faster controlled flowering response, and as indicated in chart A a shorter plant height in spring pot mum programs and a taller plant height in natural season fall programs.

In the following description color references are made to The Royal Horticultural Society Colour Chart. The color values were determined on plant material grown as a pinched garden mum grown outdoors in Salinas, Calif. on Aug. 24, 1993.

Classification:

*Botanical.*—*Dendranthema grandiflora* cv Christine.

*Commercial.*—Flat decorative spray pot mum and garden mum.

INFLORESCENCE

A. Capitulum:

*Form.*—Flat.

*Type.*—Decorative.

*Diameter across face.*—60 to 64 mm when fully opened.

B. Corolla of ray florets:

*Color (general tonality from a distance of three meters).*—Coral-red.

*Color (upper surface).*—Mature outer petals closest to 51B. Center petals closest to 51A to 51B.

*Color (under surface).*—Closest to 51C.

*Shape.*—See photograph.

C. Corolla of disc florets:

*Color (mature).*—14A.

*Color (immature).*—14A tinged with 144C.

D. Reproductive organs:

*Androecium.*—Present on disc florets only; scant pollen.

*Gynoecium.*—Present on both ray and disc florets.

PLANT

A. General appearance:

*Height.*—36 to 41 cm when grown in fall under natural daylength with no growth regulators in New Jersey, and of 15 to 20 cm when grown in 10 cm pots in spring with no growth regulator applications.

*Branching pattern.*—Spreading and prolific, with 7 to 9 breaks after pinch when grown outside under natural daylength in fall flowerings and with 5 breaks when grown in 10 cm pots for spring flowerings.

B. Foliage:

*Color (upper surface).*—147A.

*Color (under surface).*—147B.

*Shape.*—See photograph.

Chart A

COMPARISONS MADE OF PLANTS GROWN UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

| | CHRISTINE | GRENADINE |
|---|---|---|
| Ray floret color | Coral-red | Coral-bronze |
| | Flat decorative | |
| Capitulum form and type | | |
| Diameter across face of capitulum | 60 to 64 mm | 65 to 75 mm |
| | Spreading and prolific | |
| Nat. season flower date: | | |
| in Salinas, CA | Aug 24 to Sep 2 | Aug 23 to Sep 4 |
| in Hightstown, NJ | Sep 23 to Oct 5 | Sep 16 to Oct 3 |
| Controlled response | 45 to 51 days | 48 to 54 days |
| Plant height: | | |
| in natural season fall | 36 to 41 cm | 25 to 36 cm |
| in 10 cm pots spring | 15 to 20 cm | 18 to 25 cm |

I claim:

1. A new and distinct Chrysanthemum plant named Christine, as described and illustrated.

* * * * *

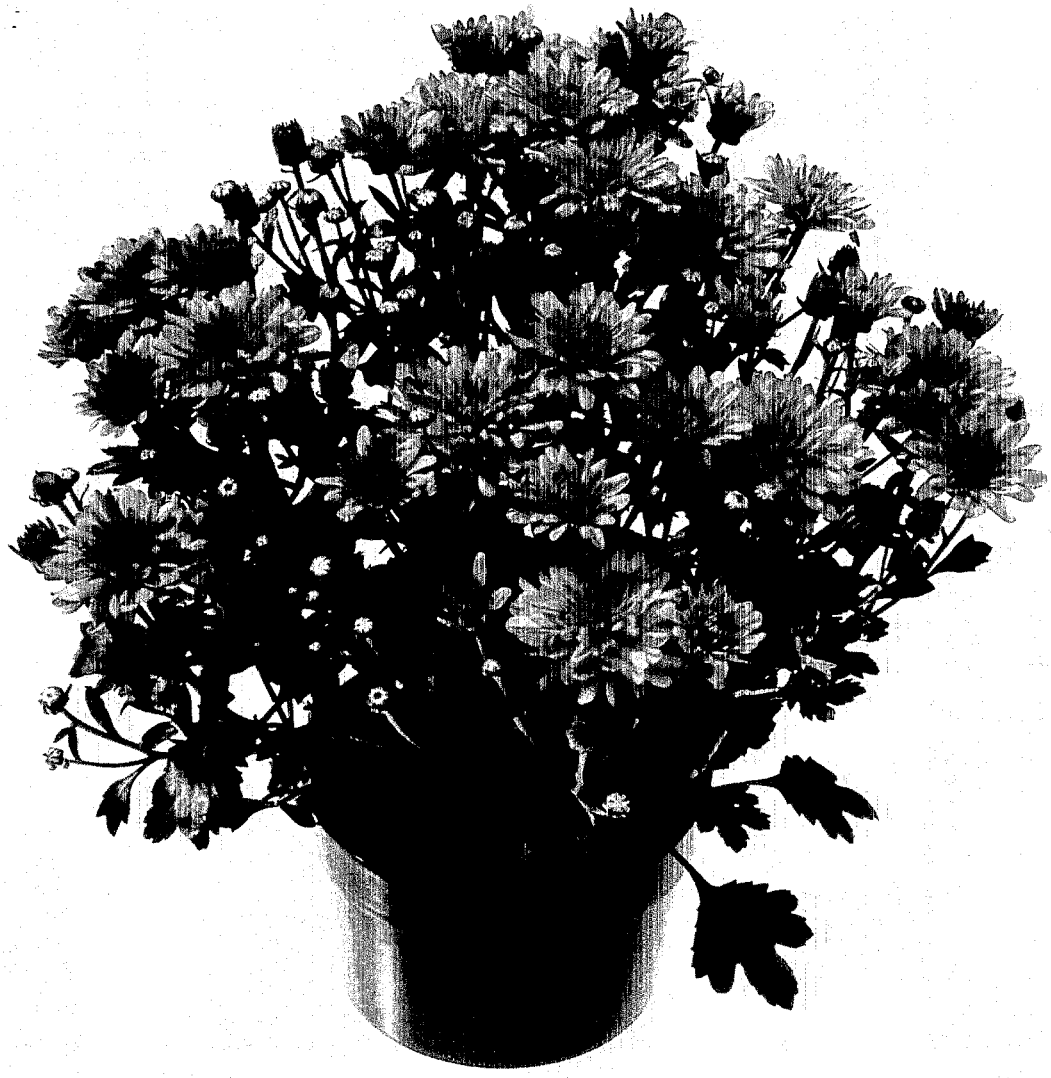

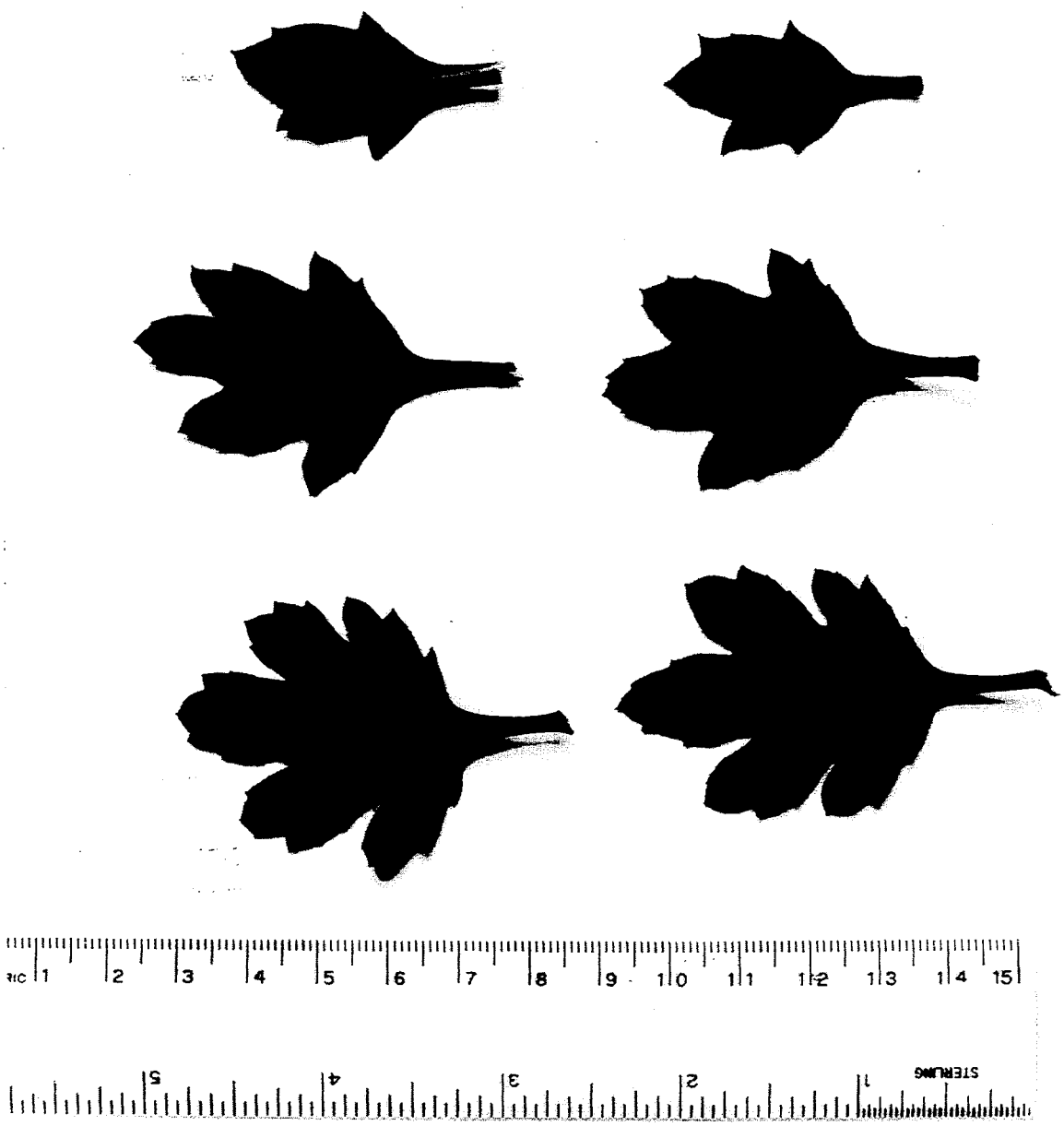

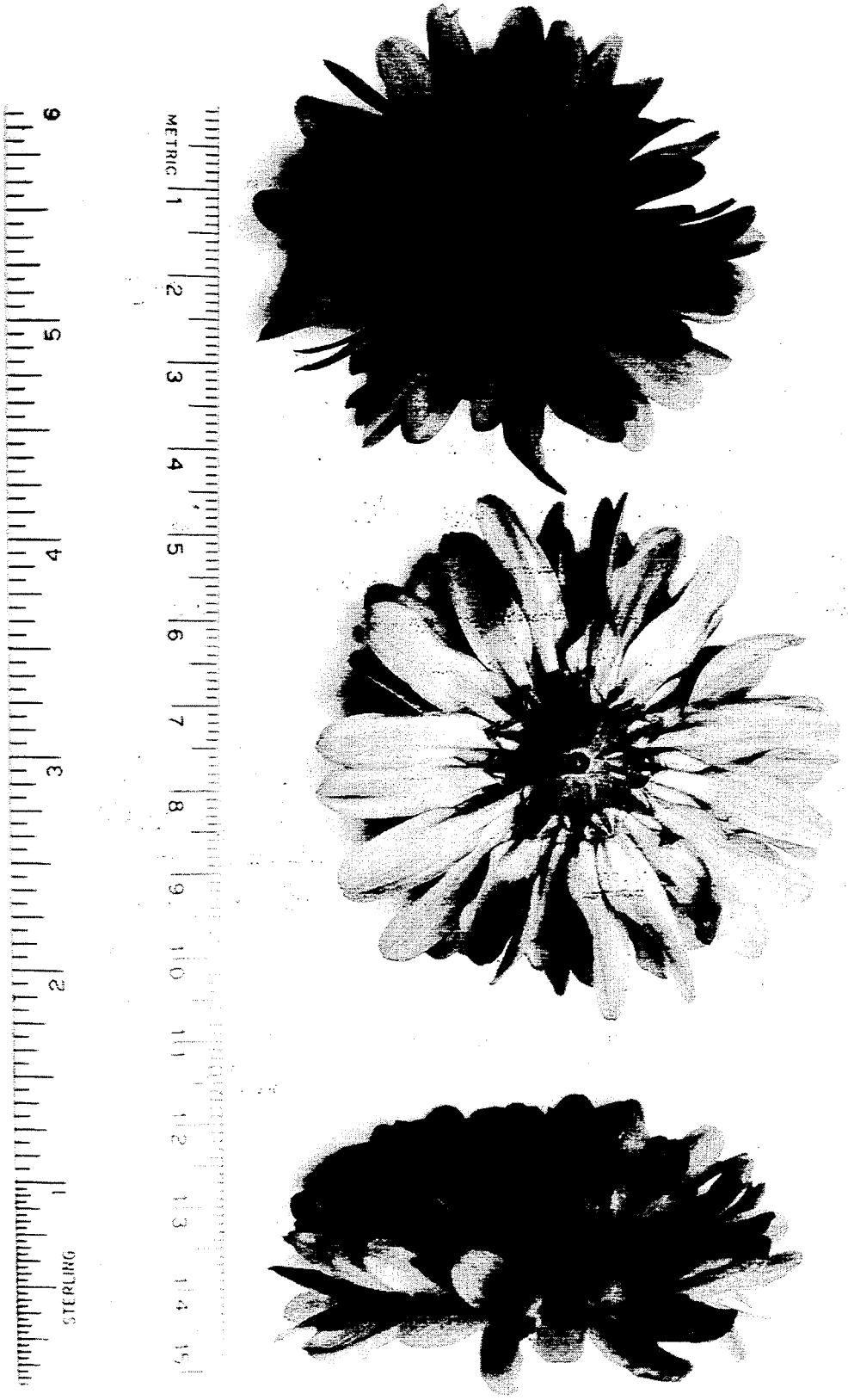
METRIC
STERLING